(12) United States Patent
Howard et al.

(10) Patent No.: US 6,649,177 B2
(45) Date of Patent: Nov. 18, 2003

(54) FORMULATIONS INCLUDING HYDROLYZED JOJOBA PROTEIN

(75) Inventors: Mark A. Howard, Atchison, KS (US); Clodualdo C. Maningat, Platte City, MO (US); Sukh Bassi, Atchison, KS (US); Dharmen Makwana, Platte City, MO (US); Soraya Rohde, Tucson, AZ (US); John Carson, Union City, NJ (US)

(73) Assignees: MGP Ingredients, Inc., Atchinson, KS (US); Desert Whale Jojoba Protein, Tucson, AZ (US)

( * ) Notice: Subject to any disclaimer, the term of this patent is extended or adjusted under 35 U.S.C. 154(b) by 32 days.

(21) Appl. No.: 09/841,544

(22) Filed: Apr. 23, 2001

(65) Prior Publication Data

US 2003/0021814 A1 Jan. 30, 2003

(51) Int. Cl.[7] .................................................. A61K 6/00
(52) U.S. Cl. ......................... 424/401; 424/59; 424/62; 424/63; 424/65; 424/69; 424/70.1; 424/78.02; 424/78.03; 424/725; 514/844; 514/880
(58) Field of Search .................. 424/400, 401, 424/78.02, 70.1, 59, 65, 725, 63; 514/844, 845, 846, 847, 848, 880

(56) References Cited

U.S. PATENT DOCUMENTS 5,547,997 A * 8/1996 Kludas .......................... 514/773
5,997,889 A * 12/1999 Durr et al. ..................... 424/401

* cited by examiner

Primary Examiner—Michael G. Hartley
Assistant Examiner—Sharmila S. Gollamudi
(74) Attorney, Agent, or Firm—Hovey Williams LLP (57) ABSTRACT

Hydrolyzed jojoba protein is provided which can be used in a variety of cosmetic formulations to enhance the desirable properties thereof. The preferred hydrolyzed jojoba protein is in the form of an aqueous dispersion containing a mixture of amino acids, peptides and/or protein fractions derived from the hydrolysis of naturally occurring jojoba protein. Cosmetic formulations such as shampoos, shampoo conditioners, hair styling gels, hair conditioners, hair reparatives, hair tonics, hair fixatives, hair mousses, bath and shower gels, liquid soaps, moisturizing sprays, makeup, pressed powder formulations, lip products, bath additives, sanitizing wipes, hand sanitizers, premoistened towelettes, skin lotions and creams, shaving creams, and sunscreens can be improved by incorporation of hydrolyzed jojoba protein therein.

11 Claims, 1 Drawing Sheet

FIG. 1.

FORMULATIONS INCLUDING HYDROLYZED JOJOBA PROTEIN

BACKGROUND OF THE INVENTION

1. Field of the Invention

The present invention is broadly concerned with hydrolyzed jojoba protein and uses thereof, particularly in connection with cosmetic products such as shampoos, shampoo conditioners, hair styling gels, hair conditioners, hair reparatives, bath and shower gels, skin lotions and creams, shaving creams, and sunscreens. More particularly, it is concerned with hydrolyzed jojoba protein which is preferably in the form of a mixture of amino acids, peptides and/or protein fractions derived from the hydrolysis of naturally occurring jojoba protein; such mixtures, when used in cosmetic products provide enhanced properties.

2. Description of the Prior Art

Jojoba is a dioecious wind-pollinated shrub, reaching a height of 1–5 meters and having a long life span (100–200 years). Jojoba is cultivated mainly in Arizona, Northern Mexico, Argentina and Israel. Genetic variability in morphology, anatomy and physiology within the species is very large and enable selection of clones for high yield and other agricultural attributes. Leaves are xerophytic with a thick cuticle, sunken stomata. They contain special tissue with a high concentration of phenol compounds. Flowers are apetalous: the female ones are usually solitary, one per two nodes although flowers every node or in clusters are not rare. The male flowers are clustered. Flower buds form in the axiles of leaves solely on the new vegetative growth occurring during the warm seasons under favorable temperatures and water regime. New flower buds are dormant and will open only after a cool season with enough cold units for the fulfillment of their chilling requirements. Anthesis occurs in the spring when the soil and air temperature rise to above 15° C. Severe water stress prevents opening of flowers. The jojoba fruit is a capsule containing one to three dark brown seeds that normally range in their dry weight between 0.5–1.1 g and contains 44–56% wax. Fruits ripen during the spring and early summer and seeds fall to the ground in late summer.

Indigenous Amerinds in the Sonora and Baja, California used jojoba seed and oil for cooking, hair care, and for treatments of many medical problems such as poison ivy, sores, wounds, colds, cancer and kidney malfunction. The oil is extracted from jojoba seed by conventional screw pressing techniques, leaving a residual defatted dry material which is high in native jojoba protein (typically on the order of 25–35% by weight protein).

Jojoba oil is a light yellow liquid at room temperature and is made up of straight-chain esters of mono-unsaturated long chain fatty acids and fatty alcohols and has an average total carbon chain length of 42 carbons. The product may be isomerized, hydrogenated, sulfurized, chlorinated or transesterified, and has a wide range of industrial uses, mainly in cosmetics in which it is incorporated in formulations for skin care preparations such as lotions, moisturizers, massage oils, creams, hair care products, lipsticks, makeups and nail products. Other potential uses include pharmaceuticals and as extenders for plastics, printers inks, gear-oil additives and lubricants.

SUMMARY OF THE INVENTION

The present invention is directed to a new form of jojoba protein, namely hydrolyzed jojoba protein and derivatives thereof, as well as uses of such protein products in cosmetic formulations. The preferred hydrolyzed jojoba protein and derivatives thereof in accordance with the invention comprise a mixture of amino acids, peptides and/or protein fractions derived from the hydrolysis of the naturally occurring jojoba protein. Such hydrolysis is preferably carried out enzymatically, but if desired acid hydrolysis can also be employed.

In more detail, the hydrolyzed jojoba protein is typically in the form of a mixture having an amino acid, peptide and/or protein fragment molecular weight range of from about 75–5,000, with an average molecular weight of from about 1,500–2,500. During processing, it is often desirable to membrane filter the hydrolysis products in order to segregate the peptides and/or protein fragments to achieve different molecular weight profiles. In one such preferred method, a hydrolyzed jojoba protein product of relatively high molecular weight is provided, with a molecular weight range for the respective peptides and/or fragments therein of from about 1,000–5,000 and with an average molecular weight of from about 3,000–4,000. Similarly, a lower molecular weight fraction (sometimes referred to as a jojoba amino acid fraction) is produced wherein the respective amino acids and peptides exhibit a molecular weight range of from about 75–1,000 with an average molecular weight of from about 100–300.

Although the hydrolyzed jojoba protein and derivatives thereof can be produced as a dry powder, this is sometimes difficult and normally the product is in the form of an aqueous dispersion containing jojoba protein or derivatives at a level of from about 18–35% by weight, more preferably from about 23–27% by weight.

As used herein, "derivatives" of hydrolyzed jojoba protein refers to changes in the structure of the individual amino acids, peptides and/or protein fragments produced by amino acid addition, deletion, replacement, substitution and/or modifications; mutants produced by recombinant and/or DNA shuffling; quaternized species; and all other chemically synthesized/modified forms of the individual amino acids, peptides and/or protein fragments which retain at least in part some activity of the initial hydrolyzed amino acids, peptides and/or protein fragments. One particularly preferred class of hydrolyzed jojoba protein derivatives is the lipid derivatives, especially those synthesized using C12–C22 fatty acids.

The term "hydrolyzed jojoba protein" is intended to embrace and cover not only the amino acids, peptides and/or protein fractions derived from the hydrolysis of naturally occurring jojoba protein but also all "derivatives" as herein defined.

The jojoba products of the invention can be used to good effect in a variety of cosmetic formulations which include at least one ingredient selected from the group consisting of humectants, emollients, conditioners, thickeners, moisturizing agents, opacifiers, pearl agents, buffering agents, slip agents, feel agents, anti-static agents, acidifiers, preservatives, film formers, plasticizers, setting agents and suspending agents (usually, each of the foregoing ingredients when used is present at a level of from about 0.05–10% by weight). An amount of hydrolyzed jojoba protein or derivative thereof is incorporated into this type of cosmetic formulation, usually at a level of from about 1–10% by weight, more preferably from about 3–8% by weight. Inasmuch as the preferred jojoba protein products are in the form of liquid dispersions, it is a simple matter to add the jojoba to the cosmetic formulations during preparation thereof.

Generally, the formulations of the invention comprise from about 10–95% by weight water, more preferably from about 20–75% by weight water.

Among the cosmetic products which can benefit from incorporation of the jojoba products of the invention are those selected from the group consisting of shampoos, shampoo conditioners, hair styling gels, hair conditioners, hair reparatives, hair tonics, hair fixatives, hair mousses, bath and shower gels, liquid soaps, moisturizing sprays, makeup, pressed powder formulations, lip products, bath additives, sanitizing wipes, hand sanitizers, premoistened towelettes, skin lotions and creams, shaving creams, and sunscreens. In products of these types, the shampoos and shampoo conditioners further comprise at least about 6% by weight detergent; the hairstyling gels further comprise a gel-forming polymer system; the hair conditioners further comprise at least about 0.3% by weight cationic hair conditioner; the hair reparatives further comprise at least about 2% by weight cationic hair conditioner; the bath and shower gels further comprise at least about 25% by weight surfactant; the skin lotions and creams further comprise at least about 2% by weight of a cream former and emollients and/or oils; the sunscreen further comprising a sunblocking agent; and the shaving creams further comprising at least about 10% by weight detergent or alternately at least about 3% by weight of a soap and having a basic pH.

DETAILED DESCRIPTION OF THE PREFERRED EMBODIMENT

The following examples set forth preferred procedures for the production of hydrolyzed jojoba protein, and use thereof in cosmetic products. It is to be understood, however, that these examples are provided by way of illustration and nothing therein should be taken as a limitation upon the overall scope of the invention.

EXAMPLE 1

This example describes a preferred procedure for the preparation of hydrolyzed jojoba protein, using solvent extracted defatted jojoba meal as a starting material. The meal is obtained from jojoba which has been conventionally press-treated with subsequent solvent extraction to remove the jojoba oil, leaving the defatted meal. The meal had a protein content of 30.2% by weight, 38.3% by weight dietary fiber, 1.7% by weight residual oil, ash of 4.3% by weight, moisture of 5.6% by weight, with the remainder being insolubles. The following table sets forth the amino acid profile of the protein fraction of the meal.

TABLE 1

| Ingredient | Amino Acid Profile |
|---|---|
| Aspartic Acid | 2.82% |
| Threonine | 1.41% |
| Serine | 1.53% |
| Glutamic Acid | 3.36% |
| Proline | 1.44% |
| Glycine | 2.45% |
| Alanine | 1.19% |
| Cystine | 0.80% |

TABLE 1-continued

| Ingredient | Amino Acid Profile |
|---|---|
| Valine | 1.54% |
| Methionine | 0.35% |
| Isoleucine | 1.03% |
| Leucine | 2.02% |
| Tyrosine | 1.07% |
| Phenylalanine | 1.23% |
| Histidine | 0.61% |
| Lysine | 1.45% |
| Arginine | 1.95% |
| Tryptophan | 0.32% |

Figure 1:
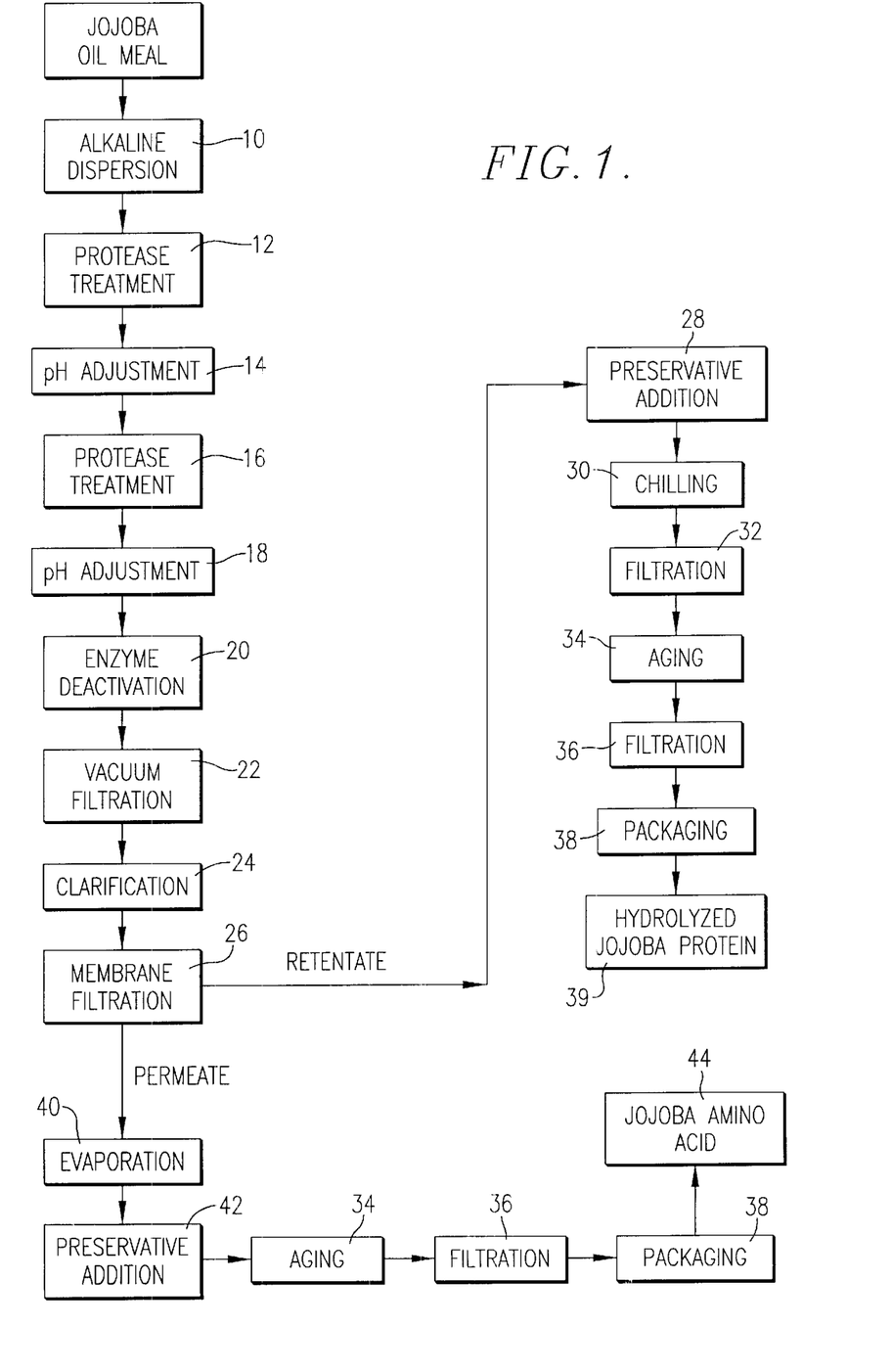
FIG. 1 is a schematic flow diagram illustrating the steps involved in the preferred process for the production of hydrolyzed jojoba protein.

The hydrolysis method is schematically illustrated in FIG. 1, and was carried out as follows. First, 750 gallons of soft water was heated to 140° F. and placed in a reaction tank. 1,000 pounds of the above-described jojoba oil meal was added to the reaction tank with agitation to completely disperse the meal. At this point, 22 pounds of 50% NaOH solution was added to the reaction tank for 1 hour to solubilize the proteins and create the alkaline dispersion 10 of FIG. 1.

In the next step, the protein slurry was treated with 15 pounds of protease enzyme (step 12), using a commercially available enzyme (Alcalase, Novo) and hydrolyzed for 2 hours with agitation. During this hydrolysis, the pH was maintained between 7.5–8.0 using 50% NaOH. A second dose of the Alcalase protease enzyme (15 pounds) was then added to the slurry followed by agitation for 2 hours. During this period, there was no pH adjustment.

In the next step 14, the pH of the slurry was adjusted to 6.5 using lactic acid, whereupon a second protease treatment (step 16) was carried out. This treatment included addition of 10 pounds of a second protease enzyme (Flavorzyme, Novo) followed by agitation for 4 hours. Thereupon, 3 pounds of Dual Protease Enzyme (Enzyme Development Corp.) was dispersed in 1 gallon of tap water and added to the slurry followed by the addition of 10 pounds of Neutrase (Novo). The slurry was then agitated for an additional 2 hours to continue the hydrolysis process.

In step 18, lactic acid was added to the slurry to lower the pH to 4.5, followed by the addition of 8 pounds sodium metabisulfite with agitation for 10 minutes. Next, in step 20, the slurry was heated to 160° F. to deactivate all protease enzymes.

The slurry containing hydrolyzed jojoba proteins was then processed in a rotary vacuum filter (step 22) to remove insolubles, and the filtrate was clarified by passage through a packed-house filter unit (step 24).

The clarified filtrate from step 24 was then fed to a nanofiltration membrane system, in order to generate a permeate and a retentate having different molecular weight profiles (step 26) after the retentate reached about 31% by weight solids using a refractometer. The membrane system was selected so that the lower molecular weight permeate proteins were generally below a molecular weight of 1,000 whereas the retentate proteins had a molecular weight of above about 1,000.

The retentate fraction was first treated by the addition of preservatives (step 28), namely 1% by weight Germaben II and 0.3% by weight Dowicil 200. The retentate was then chilled to 34–35° F. and allowed to stand for 16–24 hours (step 30). The chilled retentate was then cold-filtered in a packed-house filter unit to remove haziness (step 32), and additional preservatives were added (15% extra Germaben II and Dowicil 200).

The resulting retentate was aged 1–2 weeks (step 34), filtered (step 36), and packed in aqueous liquid form in 5-gallon jugs or 55-gallon drums (step 38) as hydrolyzed jojoba protein 39. This liquid contained about 10% by weight protein.

The permeate fraction was conventionally evaporated (step 40) to achieve a solids content of about 34% by weight, using a refractometer. Preservatives were then added (1% Germaben II and 0.3% Dowicil 200) followed by mixing for 1 hour (step 42). The permeate was then subjected to the same aging, filtration and packaging steps 34, 36 and 38 as the retentate, to produce aqueous liquid jojoba amino acid product 44. This liquid product contained about 4.5% by weight protein.

A molecular weight analysis of the hydrolyzed jojoba protein and amino acid products revealed that the higher molecular weight protein product was a mixture of peptides and/or protein fragments with a range of molecular weights of from about 1,000–5,000, and an average molecular weight of 3,500; the amino acid product was a mixture of amino acids and peptides with a range of molecular weights of from about 75–1,000, and average molecular weight of 200. In particular, the jojoba amino acid products was analyzed to contain (wb) 0.28% aspartic acid, 0.13% threonine, 0.15% serine, 0.38% glutamic acid, 0.09% proline, 0.17% glycine, 0.17% alanine, 0.03% cysteine, 0.14% valine, 0.04% methionine, 0.09% isoleucine, 0.17% leucine, <0.01% tyrosine, 0.13% phenylalanine, 0.02% histadine, 0.08% lysine, 0.11% arginine, and <0.01% tryptophan.

It will be appreciated that the two products developed using this process comprise amino acids, peptides and/or protein fragments derived from naturally occurring jojoba protein, and that the reference to "hydrolyzed jojoba protein" and "hydrolyzed jojoba amino acid" is a convenience, merely referring to the fact that the respective mixtures have different molecular weight profiles. In both cases, however, the products are "hydrolyzed jojoba protein" and this term is used herein to refer to both of these products and for that matter any product containing amino acids, peptides and/or protein fragments derived from naturally occurring jojoba protein via hydrolysis.

EXAMPLE 2

In this example, a jojoba amino acid product is produced by acid hydrolysis of jojoba meal. In the process, 450 gallons of warm (160° F.) water is transferred to a homo-mixer tank, followed by the addition of 2 gallons of concentrated HCl (36%). The mixture is stirred and 950 pounds of jojoba meal is added, with continued stirring for 30 minutes. The acidified slurry is then transferred to a glass-lined reactor and 448 gallons of concentrated HCl (36%) is added to the reactor. The temperature of the mixture within the reactor is raised to 212–220° F. using a heat exchanger, followed by mixing for 24 hours. At the end of the 24 hour mixing period, the hydrolyzate is cooled to 120–140° F., and 50% NaOH solution is added to adjust the pH to 6.0–7.0.

The neutralized hydrolyzate is then clarified using a rotary vacuum filter to remove solid particulates, and the clarified hydrolyzate is concentrated to the desired solids level (20–30%) in an evaporator.

Preservatives (1% Germaben and 0.3% Dowicil 200) are added. The product is then chilled at 34–35° F. for 16–24 hours. After chilling, the product is filtered using a packed-house filter unit to remove haziness. The product is then aged for 1–2 weeks, and a final filtration is carried out using a packed-house filter unit. The product is then packaged in suitable containers such as 5 gallon jugs or 55 gallon drums.

EXAMPLE 3

In this example, quaternized derivatives of hydrolyzed jojoba protein or jojoba amino acid are prepared. In the first step, 100 parts of the jojoba product (either hydrolyzed jojoba protein or jojoba amino acid) are added to a reaction tank. The pH of the mixture is adjusted to 9.1–9.3 using 50% NaOH.

Seventeen parts by weight of 3-chloro-2-hydroxypropyl-N,N,N-dimethyldo-decylammonium chloride (Quab 342, 40% active) and 6 parts by weight of tap water are mixed in a separate container, followed by 1.7 parts by weight of 50% NaOH with agitation. The reaction is allowed to proceed for 10 minutes, giving a final pH typically between 10–11 (a small amount of additional 50% NaOH was added if the pH fell below 10). Alternatives to the Quab 342 product are 3-chloro-2-hydroxypropyl-N,N,N-dimethyloctadecylammonium chloride (Quab 426) or 3-chloro-2-hydroxypropyl-N,N,N-trimethylammonium chloride (Quat 188) to produce other derivatives. The solution in the separate container is then added to the pH-adjusted jojoba mixture, followed by agitation for 16–24 hours. The pH of the solution is then adjusted 4.4–4.6 using lactic acid (88%) solution. The product is then filtered using a packed-house filter unit to remove particulates, followed by packaging.

Chemically, the finished product is laurdimonium hydroxypropyl hydrolyzed jojoba protein (or laurdimonium hydroxypropyl jojoba amino acid). If Quab 426 is used, the product is steardimonium hydroxypropyl hydrolyzed jojoba protein (or steardimonium hydroxypropyl jojoba amino acid). If Quat 188 is used, the product is called hydroxypropyl trimonium hydrolyzed jojoba protein (or hydroxypropyl trimonium jojoba amino acid).

EXAMPLE 4

The following products were produced using the hydrolyzed jojoba protein products 39 and 44 described in Example 1.

Moisturizing Body Wash

The following ingredients were used to prepare the body wash.

TABLE 2

| Phase | Trade Name | INCI Name | Function | Amount |
|---|---|---|---|---|
| A | Distilled Water | Distilled Water | Aqua | Adjust |
| A | Kessco EGMS 70 | Glycol Stearate | Emulsifier/Pearling Agent | 1.50 |
| A | Versene NA2 | Disodium EDTA | Chelation | 0.05 |
| A | Steol CS-230 | Sodium Laureth Sulfate | Cleaning | 20.00 |
| A | Amphosol CA | Cocamidopropyl Betaine | Foam Booster | 5.00 |
| B | Macamide C | Cocamide DEA | Foam Booster | 1.00 |
| B | Hydrolyzed Jojoba Protein | Hydrolyzed Jojoba Protein | Reparative/Moisturizer | 5.00 |
| B | Chamomile Extract | Chamomile Extract | Soothing | 0.07 |
| B | Aloe Vera Extract | Aloe Vera Extract | Healing | 0.05 |
| B | Calendula Extract | Calendula Extract | Healing | 0.05 |
| B | Glycerox HE | PEG-7 Glyceryl Cocoate | Humectant | 0.50 |
| B | Aqua Pro II ™ WGO | Wheat Germ Oil | Anti-oxidant | .50 |
| C | Preservative | QS | Antibacterial | QS |
| C | Fragrance | QS | Fragrance | QS |

The product was prepared by placing an amount of distilled water in a primary tank and heating the water to 75° C., whereupon the remaining ingredients of Phase A were added with mixing. The mixture was then cooled to 45° C. and the ingredients of Phases B and C were added with adequate mixing. The pH of the mixture was then adjusted to 5.5–6.5 using 25% citric acid, and the viscosity was adjusted using a minor amount of 10% NaCl solution.

Hair Shampoo

The following ingredients were used to prepare the shampoo.

TABLE 3

| Phase | Trade Name | INCI Name | Function | Amount |
|---|---|---|---|---|
| A | Distilled Water | Distilled Water | Aqua | Adjust |
| A | Versene NA2 | Disodium EDTA | Chelation | 0.05 |
| A | Steol CS-230 | Sodium Laureth Sulfate | Cleaning | 20.00 |
| A | Amphosol CA | Cocamidopropyl Betaine | Foam Booster | 3.00 |
| B | Macamide C | Cocamide DEA | Foam Booster | 1.00 |
| B | Hydrolyzed Jojoba Protein | Hydrolyzed Jojoba Protein | Reparative/Moisturizer | 5.00 |
| B | Chamomile Extract | Chamomile Extract | Soothing | 0.07 |
| B | Aloe Vera Extract | Aloe Vera Extract | Healing | 0.05 |
| B | Calendula Extract | Calendula Extract | Healing | 0.05 |
| C | Preservative | QS | Antibacterial | QS |
| C | Fragrance | QS | Fragrance | QS |

Distilled water was placed in a primary tank and the remaining ingredients of Phase A were added, followed by those of Phases B and C, with mixing. pH was adjusted to 5.5–6.5 using 25% citric acid, and viscosity was adjusted with 10% NaCl solution.

Ultra Shampoo

The following ingredients were used to prepare the shampoo.

TABLE 4

| Phase | Trade Name | INCI Name | Function | Amount |
|---|---|---|---|---|
| A | Distilled Water | Distilled Water | Aqua | Adjust |
| A | Merquat 550 | Polyquatemium-7 | Film Former | 0.05 |
| A | Stepanol WAC | Sodium Lauryl Sulfate | Cleansing | 10.00 |
| A | Steol CS-230 | Sodium Laureth Sulfate | Cleansing | 10.00 |
| A | Amphosol CA | Cocamidopropyl Betaine | Foam Booster | 3.00 |
| B | Mackamide C | Cocamide DEA | Foam Booster | 1.00 |
| B | Hydrolyzed Jojoba Protein | Hydrolyzed Jojoba Protein | Reparative/Substantivity | 5.50 |
| B | Chamomile Extract | Chamomile Extract | Soothing | 0.07 |
| B | Calendula Extract | Calendula Extract | Healing | 0.05 |
| C | Preservative | QS | Antibacterial | QS |
| C | Fragrance | QS | Fragrance | QS |

The ultra shampoo was prepared using the same technique for the above-described hair shampoo.

Moisturizing Shampoo

The following ingredients were used to prepare the shampoo.

TABLE 5

| Phase | Trade Name | INCI Name | Function | Amount |
|---|---|---|---|---|
| A | Distilled Water | Distilled Water | Aqua | Adjust |
| A | Merquate 550 | Polyquaternium-7 | Film Former | 0.05 |
| A | Stepanol WAG | Sodium Lauryl Sulfate | Cleansing | 10.00 |
| A | Steol CS-23 | Sodium Laureth Sulfate | Cleansing | 10.00 |
| A | Amphosol CA | Cocamidopropyl Betaine | Foam Booster | 3.00 |
| B | Mackamide C | Cocamide DEA | Foam Booster | 1.00 |
| B | Hydrolyzed Jojoba Protein | Hydrolyzed Jojoba Protein | Reparative/Moisturizer | 5.50 |
| B | Chamomile Extract | Chamomile Extract | Soothing | 0.07 |
| B | Aloe Vera Extract | Aloe Vera Extract | Healing | 0.03 |
| B | Calendula Extract | Calendula Extract | Healing | 0.05 |
| B | Licorice Extract | Licorice Extract | Astringent | 0.03 |
| C | Preservative | QS | Antibacterial | QS |
| C | Fragrance | QS | Fragrance | QS |

The moisturizing shampoo was prepared using the same technique for the above-described hair shampoo.

Hand Lotion

The following ingredients were used to prepare the hand lotion.

TABLE 6

| Phase | Trade Name | INCI Name | Function | Amount |
|---|---|---|---|---|
| A | Distilled Water | Distilled Water | Aqua | Adjust |
| A | Glycerin | Glycerin | Humectant | 1.0 |
| B | Stepan DGS SE | PEG-2 Stearate and Stearic Acid | Emulsifier | 2.00 |
| B | Lipocol C | Cetyl Alcohol | Emulsifier | 1.50 |
| B | Lipo GMS-450 | Glyceryl Stearate | Emollient | 1.50 |
| B | Shea Butter | Shea Butter | Emollient | 0.05 |
| B | Lipo IPP | Isopropyl Palmitate | Emollient | 0.80 |
| B | Lipo IPM | Isopropyl Myristate | Emollient | 0.80 |
| B | Crystosol NF 90 | Mineral Oil | Emollient | 0.50 |
| C | Skin-Flow C ™ | Calcium Starch Octenyl Succinate | Silky Feel | 6.00 |
| D | Japanese Green Tea Extract | Green Tea Extract | Astringent | 0.05 |
| D | Goldenrod Extract | Goldenrod Extract | Astringent | 0.05 |
| D | Aloe Vera | Aloe Vera | Healing | 0.05 |
| D | Yucca Extract | Yucca Extract | Stimulant | 0.03 |
| E | Jojoba Amino Acid | Jojoba Amino Acid | Moisturizer/Anti-Wrinkle | 5.00 |
| E | Preservative | QS | Antibacterial | QS |

The distilled water was placed in a mixing tank along with glycerin, and the mixture was heated to 75° C. The ingredients of Phase B were placed in a secondary tank and also heated to 75° C. Phase B was then added to Phase A at 75° C. with good agitation. The mixture was then allowed to cool to 65° C. and the ingredient of Phase C was added, making sure that there were no lumps or powder remaining on the side of the tank. The ingredients of Phase D were added in the listed order. The mixture was then cooled to 35° C. and the jojoba amino acid product 44 was added along with preservative.

Moisturizing Hand Cream

The following ingredients were used to prepare the hand cream.

TABLE 7

| Phase | Trade Name | INCI Name | Function | Amount |
|---|---|---|---|---|
| A | Distilled Water | Distilled | Aqua | QS |
| A | Propylene Glycol | Propylene Glycol | Humectant | 1.0 |
| A | Milk Protein | Completech MBAC-DS | Skin Feel | 0.50 |
| B | Stepan DGS SE | PEG-2 Stearate SE and Stearic Acid | Emulsifier | 3.00 |
| B | Lipocol C | Cetyl Alcohol | Emulsifier | 2.00 |
| B | Lipo GMS-450 | Glyceryl Sterate | Emulsifier | 1.75 |

TABLE 7-continued

| Phase | Trade Name | INCI Name | Function | Amount |
|---|---|---|---|---|
| B | Shea Butter | Shea Butter | Emollient | 0.16 |
| B | Lipo IPP | Isopropyl Palmitate | Emollient | 1.00 |
| B | Lipo IPM | Isopropyl Myristate | Emollient | 1.00 |
| B | Crystosol | Mineral Oil | Emollient | 0.50 |
| C | Skin-Flow C ™ | Calcium Starch Octenyl Succinate | Silky Feel | 6.64 |
| D | Japanese Green Tea Extract | Green Tea Extract | Astringent | 0.05 |
| D | Goldenrod Extract | Goldenrod Extract | Astringent | 0.05 |
| D | Aloe Vera | Aloe Vera | Healing | 0.05 |
| D | Yucca Extract | Yucca Extract | Stimulant | 0.03 |
| E | Jojoba Amino Acid | Jojoba Amino Acid | Anti-Wrinkle/Moisturizer | 5.00 |
| E | Preservative | QS | Antibacterial | QS |

The distilled water and other ingredients of Phase A were placed in a primary tank and heated to 75° C. The ingredients of Phase B were placed in a secondary tank and also heated to 75° C. The Phase B ingredients were added to the Phase A ingredients at 75° C. with good agitation. The mixture was then allowed to cool and at 50–55° C. the ingredient of Phase C was added, making sure that there were no lumps or powder remaining in the tank. The ingredients of Phase D were then added in the order listed. The mixture was then allowed to cool to 35° C., whereupon the jojoba amino acid product and preservative were added.

Moisturizing Foot Cream

The following ingredients were used to prepare the foot cream.

Distilled water was metered into a primary tank, followed by mixing in Cosmogel-40 with good agitation at 40° C. When the Cosmogel-40 was in solution, the remaining Phase A ingredients were added with heating to 75° C. All of the ingredients in Phase B were weighed in another tank and heated to 75° C. Phase B was then added to Phase A with good agitation, and when the temperature reached 50–55° C., the Skin-Flow-C wheat starch product was added, making sure there were no lumps or powder remaining on the side of the tank. The Phase B ingredients were then added in the listed order, followed by color addition and pH adjustment to 5.5–6.5.

Moisturizing Foundation

The following ingredients were used to prepare the foundation.

TABLE 8

| Phase | Trade Name | INCI Name | Function | Amount |
|---|---|---|---|---|
| A | Distilled Water | Distilled Water | Aqua | QS |
| A | Glycerin USP | Glycerin | Humectant | 0.5 |
| A | TEA 99% | Triethanolamine | pH adjuster | QS |
| A | Completech MBAC-DS | Milk Protein | Film forming | 0.50 |
| A | Cosmogel-40 | Wheat Starch | Thickener | 1.0 |
| B | Lipocol S | Stearyl Alcohol | Emulsifier | 3.00 |
| B | Lipocol C | Cetyl Alcohol | Emulsifier | 2.00 |
| B | Lipo GMS-450 | Glyceryl Sterate | Emulsifier | 1.75 |
| B | Aqua Pro II ™ WGO | Wheat Germ Oil | Anti-Oxidant | 0.50 |
| B | Cocobutter | Cocobutter | Emollient | .20 |
| B | Lipo IPM | Isopropyl Myristate | Emollient | .50 |
| B | Lipo IPP | Isopropyl Palmitate | Emollient | .50 |
| C | Skin-Flow C ™ | Calcium Starch Octenyl Succinate | Skin Feel | 2.00 |
| D | Calendula Extract | Calendula Extract | Healing | 0.05 |
| D | Chamomile Extract | Chamomile Extract | Astringent | 0.05 |
| D | Aloe Vera Extract | Aloe Vera Extract | Healing | 0.05 |
| D | Hydrolyzed Jojoba Protein | Hydrolyzed Jojoba Protein | Moisturizer | 5.00 |
| D | Jojoba Amino Acid | Jojoba Amino Acid | Moisturizer | 5.00 |
| D | Menthol Crystals | Menthol | Cooling | 0.20 |
| D | Peppermint Oil | Peppermint Oil | Refresher | 1.00 |
| D | Preservative | Preservative | QS | QS |
| E | Yellow #5 | FD&C Yellow #5 | QS | QS |
| E | Blue #1 | FD&C Blue #1 | QS | QS |

TABLE 9

| Phase | Trade Name | INCI Name | Function | Amount |
|---|---|---|---|---|
| A | Deionized Water | Distilled Water | Aqua | QS |
| A | TEA | Triethanolamine | Humectant | 0.5 |
| A | Propylene Glycol | Propylene Glycol | Humectant | QS |
| A | Carbomer-940 | Carbomer | Viscosity | 0.20 |
| A | Veegum | Magnesium Aluminum Silicate | Viscosity | 0.30 |
| B | Stearic Acid | Stearic Acid | Emulsifier | 1.00 |
| B | Glucamate SSE-20 | PEG-20 Methyl Glucose Sesquistearate | Conditioning | 1.00 |
| B | Ritacol 1000 | Cetearyl Alcohol and Polysorbate 60 and PEG-150 Stearate and Steareth-20 | Emulsifier | 0.80 |
| B | Lipocol C | Cetyl Alcohol | Emulsifier | 0.50 |
| B | Lipocol SC-20 | Ceteareth-20 | Emulsifier | 0.50 |
| B | Glucate SS | Methyl Glucose Sesquistearate | Emollient | .50 |
| B | Orgasol 2002 Ex | Nylon-12 | Binder | 3.50 |
| C | Isopar-G | C10–11 Isoparaffin | Solvent | 0.20 |
| D | Cab-O-Sil | Silica Dimethyl Siliylate | Bulking | 1.00 |
| D | Dow Corning 244 | Cyclomethicone | Feel | 15.00 |
| E | Eusolex T-2000 | Titanium Dioxide and Alumina and Simethicone | UV Protection | 2.00 |
| E | Iron Oxide Yellow | Iron Oxide Yellow | Color | 0.40 |
| E | Iron Oxide Black | Iron Oxide Black | Color | 0.40 |
| E | Iron Oxide Red | Iron Oxide Red | Color | 0.30 |
| F | Tween-20 | Polysorbate-20 | Surfactant | 1.00 |
| F | Hydrolyzed Jojoba Protein | Hydrolyzed Jojoba Protein | Anti-Wrinkle | 2.00 |
| F | Jojoba Amino Acid | Jojoba Amino Acid | Anti-Wrinkle | 2.00 |
| G | Skin Flow-C ™ | Calcium Starch Octenyl Succinate | Silky Feel | 2.00 |
| H | Preservative | QS | Antibacterial | QS |
| I | Fragrance | QS | Fragrance | QS |

The ingredients of Phase A were heated to 75° C., and the ingredients of Phase E were passed through a colloid mill with some propylene glycol and recirculated until the pigments were evenly dispersed. The colloid mill was rinsed with the Phase C ingredient and mixed using a lightnin mixer with heating to 75° C. Phase B components were premixed and heated to 75° C., and added to the main batch. The Phase G ingredient was then sprinkled into the main batch premix Phase D with heating to 65° C. At 40° C., the ingredients of Phase F were added to the main batch together with preservative and fragrance.

Gentle Conditioning Agent

The following ingredients were used to prepare the conditioning agent.

TABLE 10

| Phase | Trade Name | INCI Name | Function | Amount |
|---|---|---|---|---|
| A | Distilled Water | Distilled Water | Aqua | QS |
| A | Aqua Pro II ™ QWt | Hydroxypropyltrinionium Hydrolyzed Wheat Protein | Conditioning | 2.00 |
| A | Lipowax G | Stearyl Alcohol | Emulsifier | 3.50 |
| A | Lipocol C | Cetyl Alcohol (Lipo) | Emulsifier | 3.00 |
| A | Lipocol C-20 | Ceteth-20 | Emulsifier | 2.50 |
| A | Beeswax | Beeswax White | Emulsifier | 0.25 |
| A | Dimethicone | Dow Corning 200 Fluid | Feel | 1.00 |
| A | Emulsifying Wax | Stearyl Alcohol/Ceteareth-20 | Emulsifier | 1.50 |
| B | Jojoba Amino Acid | Jojoba Amino Acid | Reparative | 3.00 |
| B | Hydrolyzed Jojoba Protein | Hydrolyzed Jojoba Protein | Reparative | 3.00 |
| B | Chamomile Extract | Chamomile Extract | Soothing | 0.05 |
| B | Aloe Vera Extract | Aloe Vera Extract | Healing | 0.08 |
| B | Calendula Extract | Calendula Extract | Healing | 0.03 |
| B | Licorice Extract | Licorice Extract | Astringent | 0.08 |
| C | Preservative | QS | Antibacterial | QS |
| C | Fragrance | QS | Fragrance | QS |

Distilled water added to a primary tank followed by the ingredients of Phase A in the order listed, and the mixture was heated to 75° C. The mixture was then cooled to 35° C., and the Phase B and C ingredients were added. The pH was adjusted to 3.0 with 25% citric acid, and fragrance and preservative were added.

Moisturizing Baby Cream

The following ingredients were used to prepare the baby cream.

TABLE 11

| Phase | Trade Name | INCI Name | Function | Amount |
|---|---|---|---|---|
| A | Distilled Water | Distilled Water | Aqua | QS |
| A | Glycerin | Glycerin USP | Humectant | 2.50 |
| B | Lipocol S | Stearyl Alcohol | Emulsifier | 3.00 |
| B | Lipocol C | Cetyl Alcohol | Emulsifier | 3.50 |
| B | Lipowax G | Stearyl Alcohol | Emulsifier | 2.00 |
| B | Lipo GMS-450 | Glyceryl Sterate | Emulsifier | 2.50 |
| B | Dow Corning 200 Fluid | Dimethicone | Film Former | 1.00 |
| B | Aqua Pro ™II WGO | Wheat Germ Oil | Anti-Oxidant | 0.50 |
| C | Skin-Flow-C ™ | Calcium Starch Octenyl Succinate | Silky Feel/ Thickener | 6.50 |
| D | Hydrolyzed Jojoba Protein | Hydrolyzed Jojoba Protein | Moisturizer/ Anti-Wrinkle | 5.00 |
| F | Jojoba Amino Acid | Jojoba Amino Acid | Moisturizer/ Anti-Wrinkle | 5.00 |
| H | Preservative | QS | Antibacterial | QS |

Distilled water was metered into a primary tank and the glycerine was added with heating to 75° C. The Phase B ingredients were added in order to a secondary tank and heated to 75° C. The Phase B ingredients were added to the Phase A ingredients with good agitation. When the temperature reached 50–55° C., the Skin-Flow-C product was sifted into the batch, making sure there were no lumps or powder. The Phase D ingredients were added, and at 35° C., the preservative was added with pH adjustment to 3.5–4.5.

Anti-Wrinkle Cream

The following ingredients were used to prepare the anti-wrinkle cream.

The distilled water was added to a primary tank followed by the ingredients of Phase A, with heating to 75° C. The Phase B ingredients were added in order to a secondary tank and heated to 75° C. Phase B was added to Phase A at 75° C. with good agitation with continued mixing and cooling to 50–55° C. At 50–55° C., the Skin-Flow-C product was added, making sure there were no lumps or powder remaining. When the temperature reached 35° C., the jojoba amino acid and hydrolyzed jojoba protein were added, together with the preservative.

Hair Styling Gel

The following ingredients were used to prepare the hair styling gel.

TABLE 12

| Phase | Trade Name | INCI Name | Function | Amount |
|---|---|---|---|---|
| A | Distilled Water | Distilled Water | Aqua | QS |
| A | Glycerin | Glycerin | Humectant | 1.0 |
| A | Completech MBAC-DS | Milk Protein | Skin Feel | 0.50 |
| B | Stepan DGS SE | PEG-2 Stearate SE and Stearic Acid | Emulsifier | 3.00 |
| B | Lipocol C | Cetyl Alcohol | Emulsifier | 2.00 |
| B | Lipo GMS-450 | Glyceryl Stearate | Emulsifier | 1.75 |
| B | Promulgen D | Ceteryl Alcohol and Ceteareth-20 | Emulsifier | 1.00 |
| B | Coco Butter | Coco Butter | Emollient | 0.50 |
| B | Lipo IPP | Isopropyl Palmitate | Emollient | 1.50 |
| B | Lipo IPM | Isopropyl Myristate | Emollient | 1.50 |
| B | Crystosol NF 90 | Mineral Oil | Emollient | 0.50 |
| C | Skin-Flow-C ™ | Calcium Starch Octenyl Succinate | Silky Feel | 6.00 |
| F | Hydrolyzed Jojoba Protein | Hydrolyzed Jojoba Protein | Anti-Wrinkle | 5.00 |
| F | Jojoba Amino Acid | Jojoba Amino Acid | Anti-Wrinkle | 5.00 |
| H | Preservative | QS | Antibacterial | QS |

TABLE 13

| Phase | Trade Name | INCI Name | Function | Amount |
|---|---|---|---|---|
| A | Deionized Water | Deionized Water | Aqua | QS |
| A | Luviskol K30 | PVP | Fixative | 1.80 |
| A | TEA (25%) | Triethanolamine | pH Adjuster | QS |
| A | Carbomer-940 | Carbopol | Thickener | 1.00 |
| A | GlucamE-20 | Methyl Gluceth-20 | Film Former | 0.50 |
| A | Versene NA2 | Disodium EDTA | Chelation | 0.50 |
| B | Tween-20 | Polysorbate-20 | Cleansing | 1.50 |
| B | Uvasorb S5 | Benzophenone-4 | UV Protection | 0.04 |
| B | Hydrolyzed Jojoba Protein | Hydrolyzed Jojoba Protein | Reparative | 3.00 |
| C | Preservative | QS | Antibacterial | QS |
| C | Fragrance | QS | Fragrance | QS |

The Carbomer was added in 25% water followed by mixing in of Phase A ingredients in order. Next, the Phase B ingredients were added with good agitation, followed by addition of preservative and fragrance. The pH of the product was 5.5.

Professional Relaxer

The following ingredients were used to prepare the professional relaxer.

TABLE 14

| Phase | Trade Name | INCI Name | Function | Amount |
|---|---|---|---|---|
| A | Deionized Water | Distilled Water | Aqua | Adjust |
| A | Glycerin | Glycerin | Humectant | 6.00 |
| A | Hydrolyzed Jojoba Protein | Hydrolyzed Jojoba Protein | Reparative/Moisturizer | 5.00 |
| B | Tween-60 | Polysorbate-60 | Cleanser | 12.00 |
| B | Crystosol NF 90 | Mineral Oil | Emollient | 14.00 |
| B | Emery 1650 | Lanolin | Emollient | 1.00 |
| B | Amerchol C | Petrolatum and Lanolin and Lanolin Alcohol | Emollient | 10.00 |
| B | Lipowax G | Stearyl Alcohol and Ceteareth-20 | Emulsifier | 3.00 |
| C | Sodium Hydroxide (25%) | Sodium Hydroxide | pH Adjuster | QS |

The Phase A ingredients and Phase B ingredients were separately heated to 75° C. and mixed with good agitation. The Phase C ingredient was then added at 50–55° C. The product had a pH of 11.75–12.5.

Super Hair Reparative

The following ingredients were used to prepare the super hair reparative

TABLE 15

| Phase | Trade Name | INCI Name | Function | Amount |
|---|---|---|---|---|
| A | Distilled Water | Distilled Water | Aqua | Adjust |
| B | Hydrolyzed Jojoba Protein | Hydrolyzed Jojoba Protein | Reparative | 5.00 |
| B | Aqua Pro ™II QWs | Steardimonium Hydroxypropyl Hydrolyzed Wheat Protein | Conditioning | 3.00 |
| B | Jojoba Amino Acid | Jojoba Amino Acid | Reparative | 1.00 |
| C | Salcare SC-96 | Polyquaternium-37 and Propylene Glycol Dicaprylate/Dicaprate and PPG-1 Tridereth-1 | Emulsifier | 4.50 |
| D | Tween-20 | Polysorbate-20 | Cleanser | 1.0 |
| D | Fragrance | Fragrance | Fragrance | 0.20 |
| E | Preservative | QS | Antibacterial | QS |

The distilled water was metered into a tank, followed by the addition of the Phase B ingredients with good agitation. The Phase C ingredient was then added followed by the ingredients of Phase D and E. The pH of the product was adjusted to 3.5–4.5 with 25% citric acid.

Face Mask

The following ingredients were used to prepare the face mask.

TABLE 16

| Phase | Trade Name | INCI Name | Function | Amount |
|---|---|---|---|---|
| A | Deionized Water | Distilled Water | Aqua | Adjust |
| A | Propylene Glycol | Propylene Glycol | Humectant | 1.50 |
| B | Lipocol GMS-450 | Glyceryl Stearate | Emulsifier | 2.00 |
| B | Lipowax G | Stearyl Alcohol and Ceteareth-20 | Emulsifier | 2.50 |
| B | Lipocol C | Cetyl Alcohol | Emulsifier | 2.00 |
| C | Skin-Flow-C ™ | Calcium Starch Octenyl Succinate | Skin Feel | 2.00 |
| D | Kaoline Colloidal NF | Kaolin | Firming | 10.00 |
| D | Bentonite 670 | Bentonite | Firming | 8.00 |
| E | Aqua Pro II ™ CO | Colloidal Oatmeal | Anti-Wrinkle | 5.00 |
| E | Hydrolyzed Jojoba Protein | Hydrolyzed Jojoba Protein | Anti-Wrinkle | 3.00 |
| E | Jojoba Amino Acid | Jojoba Amino Acid | Anti-Wrinkle | 3.00 |
| F | Preservative | QS | Antibacterial | QS |

The Phase A and Phase B ingredients were separately heated to 75° C., and Phase B was added to Phase A with mixing. When the mixture reached 65° C., the Phase C ingredient was added with good mixing. Thereafter, the Phase D ingredients were added and the mixture was cooled to 35° C., whereupon the Phase E ingredients were added along with the preservative.

We claim:

1. In a cosmetic formulation including at least one ingredient selected from the group consisting of humectants, emollients, conditioners, thickeners, moisturizing agents, opacifiers, pearl agents, buffering agents, slip agents, feel agents, anti-static agents, acidifiers, preservatives, film formers, plasticizers, setting agents and suspending agents, the improvement which comprises an amount of hydrolyzed jojoba protein incorporated into the formulation.

2. The formulation of claim 1, said formulation comprising from about 10–95% by weight water.

3. The formulation of claim 2, said formulation comprising from about 20–75% by weight water.

4. The formulation of claim 1, said at least one ingredient being present at a level of from about 0.05–10% by weight.

5. The formulation of claim 1, said formulation selected from the group consisting of shampoos, shampoo conditioners, hair styling gels, hair conditioners, hair reparatives, hair tonics, hair fixatives, hair mousses, bath and shower gels, liquid soaps, moisturizing sprays, makeup, pressed powder formulations, lip products, bath additives, sanitizing wipes, hand sanitizers, premoistened towelettes, skin lotions and creams, shaving creams, and sunscreens.

6. The formulation of claim 5, each of said ingredients when used being present at a level of from about 0.05–10% by weight, and wherein:

(a) said shampoos and shampoo conditioners further comprise at least about 6% by weight detergent;

(b) said hairstyling gels further comprise a gel-forming polymer system;

(c) said hair conditioners further comprise at least about 0.3% by weight cationic hair conditioner;

(d) said hair reparatives further comprise at least about 2% by weight cationic hair conditioner;

(e) said bath and shower gels further comprise at least about 25% by weight surfactant;

(f) said skin lotions and creams further comprise at least about 2% by weight of a cream former;

(g) said sunscreen further comprising a sunblocking agent; and (h) said shaving creams further comprising at least about 10% by weight detergent and having a basic pH.

7. The formulation of claim 1, said hydrolyzed jojoba protein being present at a level of from about 1–10% by weight.

8. The formulation of claim 7, said level being from about 3–8% by weight.

9. The formulation of claim 1, said hydrolyzed jojoba protein comprising a mixture of amino acids, peptides and/or protein fractions derived from the hydrolysis of naturally occurring jojoba protein.

10. The formulation of claim 9, said mixture having a peptide and/or protein fragment molecular weight range of from about 1,000–5,000 and an average molecular weight of from about 3,000–4,000.

11. The formulation of claim 9, said mixture having an amino acid and peptide molecular weight range of from about 75–1,000 and an average molecular weight of from about 100–300.

* * * * *